(12) United States Patent
Hong et al.

(10) Patent No.: US 10,166,203 B2
(45) Date of Patent: Jan. 1, 2019

(54) PHARMACEUTICAL COMPOSITION FOR TREATING CANCER INCLUDING 2-METHOXY-4-(3-(4-METHOXYPHENYL) PROP-1-EN-1-YL)PHENOL AS ACTIVE INGREDIENT

(71) Applicant: CHUNGBUK NATIONAL UNIVERSITY INDUSTRY-ACADEMIC COOPERATION FOUNDATION, Chungcheongbuk-do (KR)

(72) Inventors: Jin-Tae Hong, Chungcheongbuk-do (KR); Hee-Pom Lee, Chungcheongbuk-do (KR); Young-Wan Ham, West Orem, UT (US); Chun-Sik Kim, Chungcheongbuk-do (KR); Heon-Sang Jung, Chungcheongbuk-do (KR)

(73) Assignee: Chungbuk National University Industry—Academic Cooperation Foundation (KR)

( * ) Notice: Subject to any disclaimer, the term of this patent is extended or adjusted under 35 U.S.C. 154(b) by 0 days.

(21) Appl. No.: 15/564,027

(22) PCT Filed: Apr. 8, 2016

(86) PCT No.: PCT/KR2016/003696
§ 371 (c)(1),
(2) Date: Oct. 3, 2017

(87) PCT Pub. No.: WO2016/163799
PCT Pub. Date: Oct. 13, 2016

(65) Prior Publication Data
US 2018/0133168 A1    May 17, 2018

(30) Foreign Application Priority Data
Apr. 10, 2015 (KR) .................. 10-2015-0050578

(51) Int. Cl.
*A61K 31/075* (2006.01)
*A61K 31/05* (2006.01)
*A61K 9/08* (2006.01)
*A61K 9/10* (2006.01)
*A61P 35/00* (2006.01)
*A61K 31/09* (2006.01)

(52) U.S. Cl.
CPC ............... *A61K 31/05* (2013.01); *A61K 9/08* (2013.01); *A61K 9/10* (2013.01); *A61K 31/09* (2013.01); *A61P 35/00* (2018.01)

(58) Field of Classification Search
CPC .................................................. A61K 31/09
USPC ......................................................... 514/721
See application file for complete search history.

(56) References Cited

U.S. PATENT DOCUMENTS 7,598,294 B2    10/2009    Potter et al.
2005/0260290 A1   11/2005   Raskin et al.

FOREIGN PATENT DOCUMENTS

KR    10-2011-0087930    8/2011

OTHER PUBLICATIONS

Hiyoshi, H. et al., "2-(4-Hydroxy-3-methoxyphenyl)-benzothiazole suppresses tumor progression and metastatic potential of breast cancer cells by inducing ubiquitin ligase CHIP", Scientific Reports, 4:7056, 11 pages (2014).
International Search Report from PCT/KR2016/00396.
Pathak, et al., "Synthesis of 2-methoxyestradiol and eugenol template based diarylpropenes as non-steroidal anticancer agents", RSC Adv., 4:35171-35185 (2014).

*Primary Examiner* — Shengjun Wang
(74) *Attorney, Agent, or Firm* — JHK Law; Joseph Hyosuk Kim

(57) ABSTRACT

The present disclosure relates to an anticancer use of a novel compound, i.e., 2-methoxy-4-(3-(4-methoxyphenyl)propyl-1-en-1-yl)phenol. The compound of the present disclosure effectively inhibits the growth of cancer cells and tumors in vitro and in a xenograft animal model. The compound of the present disclosure illustrates an anticancer activity by inhibiting a DNA binding activity of transcription factor STAT 3 in cancer cells, inducing apoptosis of cancer cells, and reducing the expression of a cell cycle regulatory protein. The compound of the present disclosure can be developed as an active ingredient of a strong anticancer drug.

9 Claims, 3 Drawing Sheets

[FIG 1]
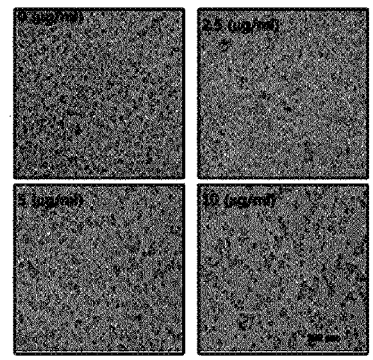
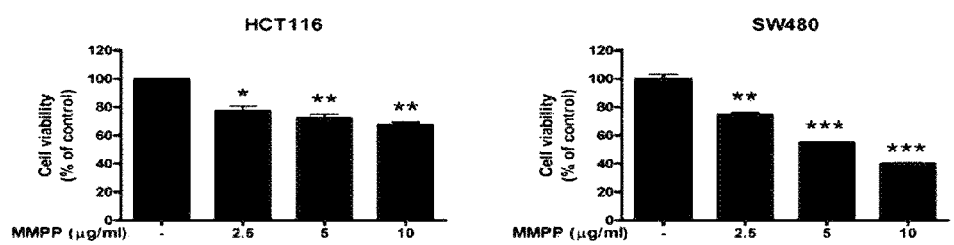

[FIGURE 2]
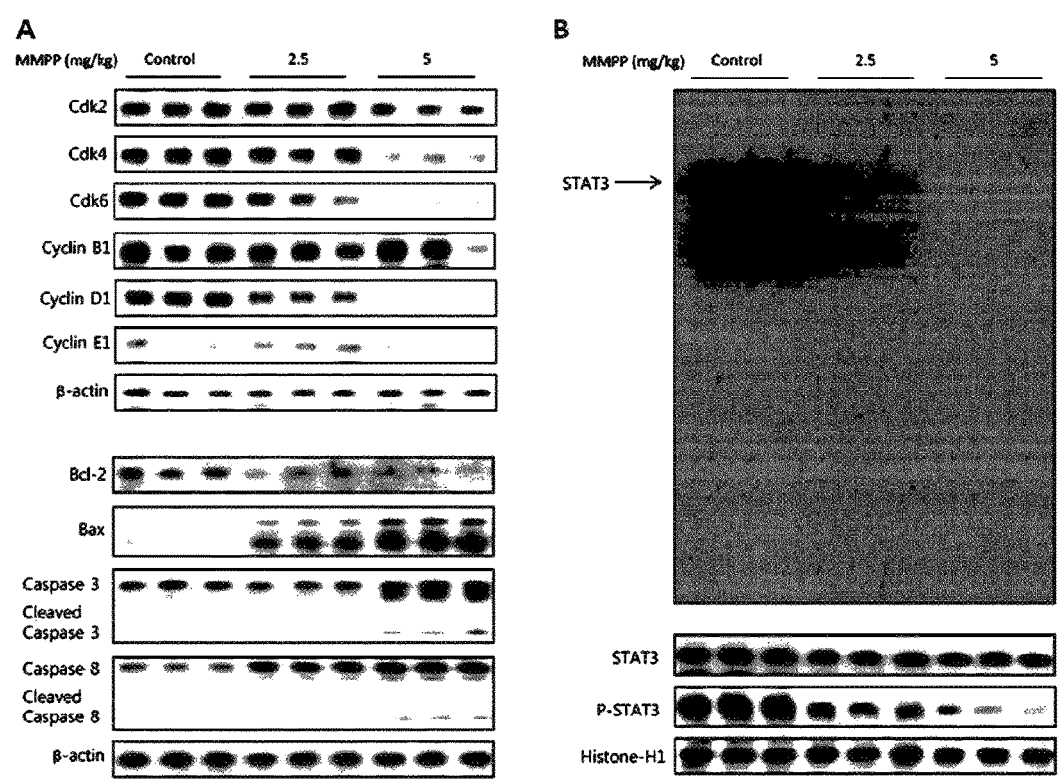

[FIG 3]
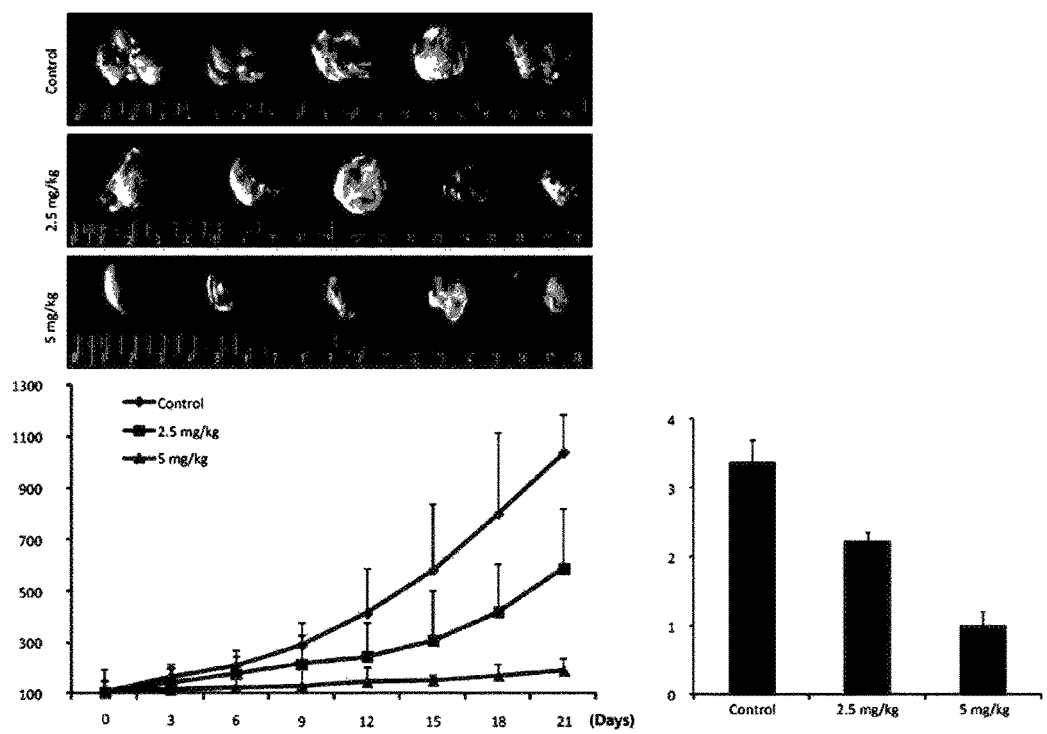

PHARMACEUTICAL COMPOSITION FOR TREATING CANCER INCLUDING 2-METHOXY-4-(3-(4-METHOXYPHENYL) PROP-1-EN-1-YL)PHENOL AS ACTIVE INGREDIENT

TECHNICAL FIELD

The present disclosure relates to a pharmaceutical composition for treating cancer including 2-methoxy-4-(3-(4-methoxyphenyl)propyl-1-en-1-yl)phenol (MMPP) as an active ingredient.

BACKGROUND ART

NF-κB is a protein family involved in the regulation of inflammatory response, immune modulation, apoptosis, cell proliferation, epithelial differentiation, and the like. It regulates the expression of various genes and forms the central axis of the intracellular signaling system. NF-κB increases important substances related to cell proliferation, apoptosis, and cell cycle as well as signaling substances of inflammation and immune response. Such disorder of regulation of NF-κB activation pathway causes continuous increase of these mediators, and the condition becomes similar to autoimmune diseases. In addition, NF-κB plays an important role in maintaining oncogenic phenotype by participating in regulation of genes involved in cell proliferation, survival-related genes and angiogenesis, and metastasis. In fact, the sustained expression of NF-κB plays an important role in tumorigenesis and therapy, given that increased NF-κB activity after chemotherapy induces apoptosis suppression and reduces the therapeutic effect of anticancer drugs. It has been revealed that the activity of NF-κB is increased in epithelial cell carcinoma, carcinoma cell line, lymphoma and the like, which means that apoptosis is inhibited and cell proliferation rate and metastasis can be increased. It is known that NF-κB-activated tumors do not respond well to anticancer drugs. As a cause, P-glycoprotein, which causes multidrug resistance, is thought to be the genes regulated by NF-κB. In contrast, inhibition of NF-κB activation in fibrosarcoma, colorectal cancer, and rectal cancer cell lines resulted in a favorable outcome for radiation therapy or chemotherapy treatment by creating an environment where apoptosis is likely to occur easily.

Activation of NF-κB proliferates blood vessels via vascular endothelial growth factor (VEGF), COX-2 and iNOS, and is involved in tumor invasion and metastasis through matrix metalloproteinase, plasminogen activator, heparinase (Heparinase), and the like.

On the other hand, together with NF-κB, STAT3 is also an important transcription factor associated with inflammatory and immune responses. STAT3 (signal transducer and activator of transcription3) is a protein in the cytoplasm that is not activated. It binds to the DNA sequence as part of a group called 'DNA binding factor', and regulates the transcription process of transferring genetic information from DNA to RNA. Activation of STAT3 is accomplished by phosphorylation of tyrosine residues in the STAT3 transactivation domain by a variety of growth factors and cytokines. This phosphorylated STAT3 (p-STAT3) enters the nucleus and induces the expression of a wide range of target genes involved in inflammatory responses and tumorigenesis. In addition to the association with STAT3 and arthritis, STAT3 also affects the mechanism of cancer development and treatment. STAT3 is the only molecule that regulates the genes involved in the initiation and promotion of cancer. STAT3 acts as the first step in cancer development progress stage. In addition, the STAT3 is a transcription factor protein. The role of STAT3 is a signal transduction activation factor that leads to cancer by inadequately sending an external signal to differentiate healthy cells, in addition to wound treatment, which is associated with tumorigenesis. Yu H. et al. indicate that sustained activation of STAT3 mediates inflammatory responses that promote tumors, while STAT3, which is activated at all times, and some STAT5 increase tumor cell proliferation, survival and invasion while inhibiting anti-tumor immune action. That is, a transient inflammatory signal can activate an epigenetic switch that converts unmodified cells into cancer cells through a positive feedback loop such as NF-κB, Lin28, Let-7, and IL-6. At this time, STAT3 transcription factor activated by the IL-6 directly activates microRNAs such as miR-21 and miR-181b-1, which inhibit PTEN (phosphatase and tensin homolog) and CYLD (cylindromatosis) tumor suppressor, and induces NF-κB activation increase.

That is, STAT3 is a part of the positive feedback loop that is the basis of the epigenetic switch that links inflammation to cancer with the cytokines such as miR-21, miR-181b-1, PTEN and CYLD.

In addition, STAT3 is always activated in a wide range of tumors, including colorectal cancer, colon cancer, liver cancer, breast cancer, prostate cancer, multiple myeloma, and glioblastoma. This is because tumor cells depend on STAT3 to sustain growth and avoid apoptosis.

The patent documents and references mentioned herein are incorporated herein by reference to the same extent as if each reference is individually and clearly specified by reference.

DISCLOSURE

Technical Problem

The present inventors have successfully synthesized 2-methoxy-4-(3-(4-methoxyphenyl)propyl-1-en-1-yl)phenol capable of controlling the activity of NF-κB, IKK and STAT3, and tried to develop an effective cancer treatment agent using this compound. As a result, the inventors have experimentally verified that the compound inhibits the DNA binding activity of STAT3 in cancer cells, induces apoptosis, reduces the expression of cell cycle regulatory proteins, and effectively inhibits the growth of cancer cells and tumors in vitro and in a xenograft animal model, and completed the present disclosure.

Accordingly, an object of the present disclosure is to provide a pharmaceutical composition for treating cancer including 2-methoxy-4-(3-(4-methoxyphenyl)propyl-1-en-1-yl)phenol (MMPP) as an active ingredient.

Other objects and technical features of the present disclosure will be described in more detail by the following detailed description of the invention, claims and drawings.

Technical Solution

According to one aspect of the present disclosure, there is provided a pharmaceutical composition for treating or preventing cancer including a pharmaceutically effective amount of a compound represented by the following formula 1; and a pharmaceutically acceptable carrier.

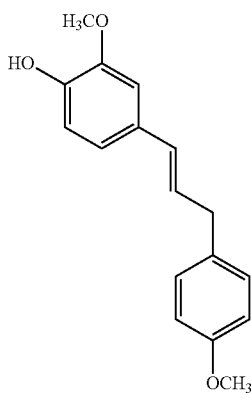

[Formula 1]

The compound of the formula 1 has a molecular formula of $C_{17}H_{18}O_3$ and is formally called "2-methoxy-4-(3-(4-methoxyphenyl)propyl-1-en-1-yl)phenol." Herein, it is abbreviated as "MMPP."

The compound of the formula 1, which is an active ingredient of the composition of the present disclosure, has an anticancer activity that inhibits the growth of cancer cells.

The compound of the present disclosure inhibits the DNA binding activity of the transcription factor, STATS (signal transducer and activator of transcription 3). STAT3 is a member of protein of the STAT family, and acts as a transcription activator that activates transcription of a gene in response to cytokines or growth factors.

The STAT3 protein is active in most cancer cells and is known to be involved in the proliferation and invasion of cancer cells.

The compound of the present disclosure induces apoptosis of cancer cells. The compound of the present disclosure increases the expression of pro-apoptotic proteins and reduces the expression of anti-apoptotic proteins.

According to an embodiment of the present disclosure, the pro-apoptotic proteins are cleaved caspase-3, cleaved caspase-8 or Bax protein.

According to another embodiment of the present disclosure, the anti-apoptotic protein is a Bcl-2 protein.

The compound of the present disclosure reduces the expression of cell cycle regulatory proteins.

According to another embodiment of the present disclosure, the cell cycle regulatory protein is Cdk (cyclin-dependent kinase) 2, Cdk (cyclin-dependent kinase) 4, Cdk (cyclin-dependent kinase) 6, cyclin B1, cyclin D1, or cyclin E1.

Cancer, which is a target disease for treatment by the pharmaceutical composition of the present disclosure, is a generic term for diseases caused by cells having aggressive characteristics in which the cells ignore normal growth limits and divide and grow, invasive characteristics to penetrate surrounding tissues, and metastatic characteristics that spread to other sites in the body.

According to a preferred embodiment of the present disclosure, the target cancer for treatment is breast cancer, lung cancer, stomach cancer, liver cancer, blood cancer, bone cancer, pancreatic cancer, skin cancer, head and neck cancer, skin or ocular melanoma, uterine sarcoma, ovarian cancer, rectal cancer, anal cancer, colorectal cancer, colon cancer, tubal cancer, endometrial cancer, cervical cancer, small bowel cancer, endocrine cancer, thyroid cancer, parathyroid cancer, kidney cancer, soft tissue tumor, urethral cancer, prostate cancer, bronchial cancer or bone marrow cancer, but is not limited thereto.

The composition of the present disclosure is provided in the form of a pharmaceutical composition comprising (i) a pharmaceutically effective amount of a compound represented by the above-described formula (1); and (ii) a pharmaceutically acceptable carrier.

The term "pharmaceutically effective amount" means an amount that is sufficient and appropriate to exert a substantial anticancer effect when the compound of the present disclosure is administered in vivo as a pharmaceutically active ingredient.

The term "pharmaceutically acceptable" means that it does not cause an allergic reaction or similar adverse reaction when administered to a human.

The pharmaceutically acceptable carriers included in the pharmaceutical composition of the present disclosure are those conventionally used in the preparation and include lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrup, methylcellulose, methylhydroxybenzoate, propylhydroxybenzoate, talc, magnesium stearate and mineral oil, and the like, but are not limited thereto.

The pharmaceutical composition of the present disclosure may further include, in addition to the above ingredients, a lubricant, a wetting agent, a sweetening agent, a flavoring agent, an emulsifier, a suspending agent, a preservative and the like. Suitable pharmaceutically acceptable carriers and preparations are described in detail in *Remington's Pharmaceutical Sciences* (19th ed., 1995).

The appropriate dosage of the pharmaceutical composition of the present disclosure may be prescribed by various methods depending on factors such as the preparation method, administration method, age, body weight, sex, pathological condition of a patient, food, administration time, administration route, excretion speed and response susceptibility. Meanwhile, the dosage of the pharmaceutical composition of the present disclosure is preferably 0.001 to 100 mg/kg (body weight) per day.

The pharmaceutical composition of the present disclosure may be administered orally or parenterally, and when administered parenterally, it may be administered by intravenous injection, subcutaneous injection, muscle injection, intraperitoneal injection, transdermal administration, or the like.

The concentration of the active ingredient included in the composition of the present disclosure is determined in consideration of the purpose of treatment, the condition of a patient, the period of time required, the severity of disease, and the like, but is not limited to a specific range of concentration.

The pharmaceutical composition of the present disclosure may be prepared in a unit dosage form by preparing it with a pharmaceutically acceptable carrier and/or excipient according to a method which can be easily carried out by a person having ordinary skill in the technical field to which the present disclosure pertains, or may be prepared by including it into a multi-dose container. The formulations may be in the form of solutions, suspensions or emulsions in oils or aqueous media, or in the form of extracts, powders, granules, tablets or capsules, and may additionally include dispersing or stabilizing agents.

Advantageous Effects

The features and advantages of the present disclosure are summarized as follows:

(i) The present disclosure relates to an anticancer use of the novel compound 2-methoxy-4-(3-(4-methoxyphenyl)propyl-1-en-1-yl)phenol.

(ii) The compound of the present disclosure effectively inhibits the growth of cancer cells and tumors in vitro and in a xenograft animal model.

(iii) The compound of the present disclosure inhibits the DNA binding activity of the transcription factor STATS in cancer cells, induces apoptosis of cancer cells, and inhibits the expression of cell cycle regulatory proteins, thereby exhibiting an anticancer activity.

(iv) The compound of the present disclosure may be developed as an active ingredient of strong anticancer agents.

DESCRIPTION OF DRAWINGS

FIG. 1 illustrates the results of inhibition of the growth of SW480 cell line in dependence on the concentration of MMPP. The upper right panel illustrates cell photos exhibiting the results of inhibition of the growth of SW480 cells in dependence on the concentration of MMPP. The lower right panel illustrates the effect of MMPP on the colon cancer cell line SW480.

FIG. 2 illustrates the results of changes in the expression of cell cycle regulatory proteins and apoptotic signal proteins by MMPP. The upper part of panel A of FIG. 2 illustrates the result that the expression of the cell cycle regulatory signal protein is reduced by MMPP. The lower part of panel A of FIG. 2 illustrates the results of an increase in expression of pro-apoptotic protein and a decrease in expression of anti-apoptotic protein. Panel B of FIG. 2 illustrates the results of inhibition of DNA binding activity of STAT3 by MMPP.

FIG. 3 illustrates the results of MMPP inhibition of colon cancer growth in a xenograft model.

MODES OF THE INVENTION

EXAMPLE

Experimental Materials and Methods

1. Cell Culture

The human colon cancer cell line, SW480, was purchased from the American Type Culture Collection (Manassas, Va., USA) and cultured in an RPMI (Roswell Park Memorial Institute)-1640 medium (Gibco-BRL) to which 10% heat-inactivated fetal bovine serum (FBS) and penicillin/streptomycin at 37° C. humidified atmosphere of 5% $CO_2$. The cells were cultured in a 100 mm culture dish at a concentration of $4 \times 10^5$ cells for experiments.

2. Cell Viability Analysis Using MTT Assay

The influence of 2-methoxy-4-(3-(4-methoxyphenyl) prop-1-en-1-yl)phenol (MMPP) on the viability of cells was confirmed by colorimetric and metabolic activity assay using MTT [3-(4,5-dimethylthiazol-2-yl)-2,5-diphenyltetrazolium bromide]. Put briefly, cells were inoculated on 96-well plates at $1 \times 10^4$ cells/well and cultured for 24 hours. Cells were treated with 2.5 to 10 μg/ml MMPP or DMSO (dimethyl sulfoxide), a solvent for MMPP. After culturing for 24 hours, the medium including MMPP was removed and replaced with 100 μl of fresh medium. After culturing for 1.5 hours, medium including MTT was removed and 200 μl DMSO was added to each well. The plate was then agitated at a weak intensity until the color reaction of the plate became uniform. Colorimetric evaluation was performed using a microplate reader at 540 nm.

3. Western Blot Analysis

Lysates, cytosolic and nuclear extracts of whole cells were obtained. SDS-PAGE and western blot analysis were performed as described in published documents 1 and 2 [1, 2]. Put briefly, the cells of $5 \times 10^5$ cells/well were inoculated in 6-well plates and cultured for 24 hours. Cells were then treated with MMPP or DMSO for 24 hours. The treated cells were washed twice with PBS and lysed. Proteins from the lysed cells were separated on 10 to 15% SDS-PAGE. Proteins were transferred to a PVDF membrane and the PVDF membrane was blocked with TBS/T-buffer including 5% defatted milk for 2.5 hours at room temperature. The membrane to which the proteins are transferred was analyzed by using a mouse monoclonal antibody for as a primary antibody. Protein expression was visualized using a chemiluminescence reagent (Amersham Pharmacia Biotech, Inc., Buckinghamshire, UK) and measured using a in which a CCD camera (Fusion-FX, Fisher BioTech, Ltd., Wembley, Australia) is installed.

4. Analysis of DNA Binding Activity of STAT3 Using EMSA

The DNA binding activity of STAT3 was measured using an electrophoretic mobility shift assay (EMSA) as described in document 1. Put briefly, cells were cultured in a 100 mm culture dish at 37° C. for 24 hours and then treated with MMPP or DMSO. After incubation for 24 hours, the cells were washed three times with cold PBS and nuclear extracts for EMSA experiments were prepared. Relative thickness of the DNA-protein binding band was quantified using Lab Works 4.0 software (UVP Inc., Upland, Calif., USA) after scanning with densitometry.

5. Anticancer Activity Research of a Xenograft Animal Model 6-week-old BALB/c athymic nude mouse was purchased from Japan SLC. The mice were bred and maintained in accordance with the Aseptic Environment certified by the American Association for Accreditation of Laboratory Animal Care and the standards and regulations established by the Ministry of Food and Drug Safety. Human colon cancer cell line SW620 was injected subcutaneously ($1 \times 10^7$ cancer cells/0.1 ml PBS/animal) into the lower flank of host mice using a 27-gauge needle. When the mean tumor volume was 300 to 400 $mm^3$ after 20 days, MMPP dissolved in 0.01% DMSO were injected intraperitoneally (2.5 mg/kg and 5 mg/Kg) into tumor bearing mice twice a week for 3 weeks. The group treated with 0.01 mol/L of DMSO was used as a negative control group.

The weight of the mice and the tumor volume were observed twice a week. The volume of the tumor was calculated and computed by the equation: $(A \times B^2)/2$ after measuring with vernier calipers. In the above equation, A and B mean the long and short lengths of the tumor, respectively. At the end of the experiment, mice were sacrificed by cervical dislocation. The tumor was surgically removed and separated from the muscles and skin surrounding the tumor, and then the weight was measure.

Experiment Results

1. Effect of MMPP on Growth of Human Colon Cancer Cells

The inhibitory effect of MMPP on the growth of human colon cancer cells was examined using SW480 cells. As illustrated in FIG. 1, when MMPP (2.5 to 10 μg/ml) was treated for 24 hours, MMPP inhibited the growth of SW480 cells in a concentration-dependent manner, and the $IC_{50}$ value was 5.9 μg/ml. In addition, it was confirmed that MMPP significantly reduced cell density as compared to the control group of SW480 cells. These results indicate that MMPP has a strong inhibitory effect on the growth of colon cancer cells.

2. Effect of MMPP on Cell Cycle Regulatory Signal and Apoptosis Signal In order to investigate the basic mechanism of the growth inhibitory effect of colon cancer cells of MMPP, it was examined whether MMPP treatment affects cell cycle regulation and apoptosis signals in SW480 cells. As illustrated in panel A of FIG. 2, the treatment of MMPP effectively reduced the expression of cell cycle regulatory signal proteins. In addition, MMPP increased the expression of cleaved caspase-3, cleaved caspase-8 and Bax, which are pro-apoptotic proteins, but reduced the expression of the anti-apoptotic proteins Bcl-2 (Panel A of FIG. 2).

3. Effect of MMPP on STAT3 DNA Binding Activity

In order to determine whether MMPP reacted with STAT3 to inhibit DNA binding activity of STAT3, MMPP was exposed to SW480 cells for 1 hour and the DNA binding activity of STAT3 was measured. As a result of the experiment, it was confirmed that MMPP effectively inhibited DNA binding activity of STAT3 in SW480 cells (panel B in FIG. 2).

4. Effect of MMPP on Growth of Colon Cancer in a Xenograft Model

In order to confirm the anticancer effect in vivo, nude mice with xenografted colon cancer were treated with MMPP and tumor growth was investigated. In a SW480 xenografted mouse study, mice with a tumor volume of 100 to 300 mm$^3$ were injected via intraperitoneal injection of MMPP twice a week for 3 weeks. Tumor volumes of mice treated with 2.5 mg/kg and 5 mg/kg of MMPP were 65% and 35%, respectively, compared to the control group (FIG. 3). In the same manner as an in vitro experimental result, these results suggest that MMPP inhibits the growth of colon cancer in vivo.

The specific embodiments described herein are representative of preferred embodiments or examples of the present disclosure, and thus the scope of the present disclosure is not limited thereto. It will be apparent to those skilled in the art that modifications and other uses of the present disclosure do not depart from the scope of the invention described in the claims.

The invention claimed is:

1. A method for treating cancer, comprising administering to a subject in need thereof pharmaceutical composition comprising a pharmaceutically effective amount of a compound represented by the following formula 1; and a pharmaceutically acceptable carrier

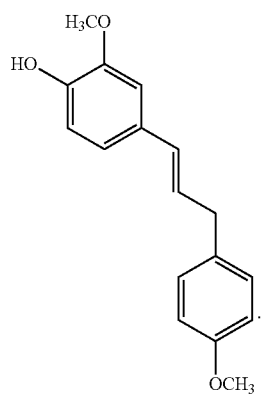

[Formula 1]

2. The method of claim 1, wherein the compound represented by the formula 1 increases the expression of a pro-apoptotic protein in cancer cells.

3. The method of claim 2, wherein the pro-apoptotic protein is cleaved caspase-3, cleaved caspase-8 or Bax protein.

4. The method of claim 1, wherein the compound represented by the formula 1 reduces the expression of an anti-apoptotic protein in cancer cells.

5. The method of claim 4, wherein the anti-apoptotic protein is a Bcl-2 protein.

6. The method of claim 1, wherein the compound represented by the formula 1 reduces the expression of a cell cycle regulatory protein.

7. The method of claim 6, wherein the cell cycle regulatory protein is Cdk (cyclin-dependent kinase) 2, Cdk (cyclin-dependent kinase) 4, Cdk (cyclin-dependent kinase) 6, cyclin B1, cyclin D1, or cyclin E1.

8. The method of claim 1, wherein the cancer is selected from the group consisting of breast cancer, lung cancer, stomach cancer, liver cancer, blood cancer, bone cancer, pancreatic cancer, skin cancer, head and neck cancer, skin or ocular melanoma, uterine sarcoma, ovarian cancer, rectal cancer, anal cancer, colorectal cancer, colon cancer, tubal cancer, endometrial cancer, cervical cancer, small bowel cancer, endocrine cancer, thyroid cancer, parathyroid cancer, kidney cancer, soft tissue tumor, urethral cancer, prostate cancer, bronchial cancer or bone marrow cancer.

9. A method for treating cancer by inhibiting DNA binding activity of transcription factor STAT3, comprising administering to a subject in need thereof pharmaceutical composition comprising a pharmaceutically effective amount of a compound represented by the following formula 1; and a pharmaceutically acceptable carrier

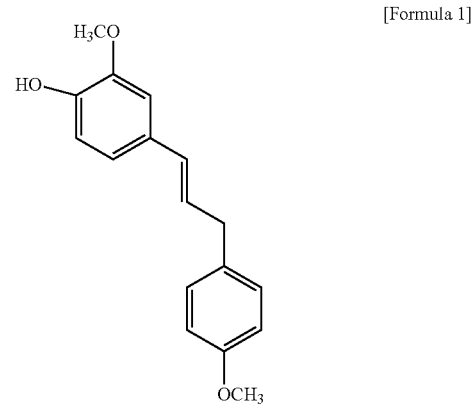 [SMILES: COc1ccc(C/C=C/c2ccc(O)c(OC)c2)cc1]

[Formula 1]

* * * * *